US012669168B2

(12) United States Patent
Sorgenfrei et al.

(10) Patent No.: US 12,669,168 B2
(45) Date of Patent: Jun. 30, 2026

(54) ROBOTIC PRONATOR

(71) Applicant: The Regents of the University of Michigan, Ann Arbor, MI (US)

(72) Inventors: Evelyn Sorgenfrei, Ann Arbor, MI (US); Vasil Iakimovitch, Ann Arbor, MI (US); Revanth Damerla, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 143 days.

(21) Appl. No.: 18/531,916

(22) Filed: Dec. 7, 2023

(65) Prior Publication Data
US 2024/0191791 A1 Jun. 13, 2024

Related U.S. Application Data

(60) Provisional application No. 63/430,785, filed on Dec. 7, 2022.

(51) Int. Cl.
*F16H 37/12* (2006.01)
*A61F 2/58* (2006.01)
(Continued)

(52) U.S. Cl.
CPC ........... *F16H 37/122* (2013.01); *A61F 2/585* (2013.01); *B25J 9/106* (2013.01); *B25J 9/123* (2013.01);
(Continued)

(58) Field of Classification Search
CPC .. F16H 37/122; A61F 2/585; A61F 2002/701; A61F 2002/704; B25J 9/106; B25J 9/123
See application file for complete search history.

(56) References Cited

U.S. PATENT DOCUMENTS

| | | | |
|---|---|---|---|
| 6,361,570 B1 | 3/2002 | Gow | |
| 8,747,486 B2 | 6/2014 | Kawasaki et al. | |

(Continued)

FOREIGN PATENT DOCUMENTS

| | | |
|---|---|---|
| CN | 201743884 U | 2/2011 |
| CN | 102621997 B | 10/2013 |

(Continued)

OTHER PUBLICATIONS

Ahmad et al., Bowden Cable Based Powered Ball and Socket Wrist Actuator. World Academy of Science, Engineering and Technology, 2012, 69, 4 pages.

(Continued)

*Primary Examiner* — Victor L Macarthur
(74) *Attorney, Agent, or Firm* — Casimir Jones, S.C.; Brian F. Bradley

(57) ABSTRACT

An assembly comprising a crank configured to rotate about an output axis; a first motor configured to rotate a first screw; and a first nut assembly configured to translate along the first screw in response to rotation of the first screw. The first nut assembly is coupled to the crank. The assembly further includes a second motor configured to rotate a second screw; and a second nut assembly configured to translate along the second screw in response to rotation of the second screw. The second nut assembly is coupled to the crank. Translation of the first nut assembly along the first screw is out of phase with translation of the second nut assembly along the second screw.

27 Claims, 13 Drawing Sheets

(51) Int. Cl.
  *B25J 9/10* (2006.01)
  *B25J 9/12* (2006.01)
  *A61F 2/70* (2006.01)

(52) U.S. Cl.
  CPC ... *A61F 2002/701* (2013.01); *A61F 2002/704* (2013.01)

(56) References Cited

U.S. PATENT DOCUMENTS

| | | | |
|---|---|---|---|
| 8,979,943 B2 | 3/2015 | Evans et al. | |
| 9,403,056 B2 | 8/2016 | Weinberg et al. | |
| 10,357,381 B2 * | 7/2019 | Kuiken | A61F 2/60 |
| 10,369,024 B2 | 8/2019 | Gill | |
| 10,471,610 B2 | 11/2019 | Han et al. | |
| 2009/0326677 A1 | 12/2009 | Phillips et al. | |
| 2015/0257903 A1 * | 9/2015 | Perry | A61F 2/54 623/24 |
| 2019/0343705 A1 | 11/2019 | Bonutti et al. | |
| 2019/0380846 A1 | 12/2019 | Lipsey et al. | |
| 2020/0375761 A1 | 12/2020 | Iversen et al. | |
| 2021/0177626 A1 | 6/2021 | Kuiken et al. | |
| 2021/0236306 A1 | 8/2021 | Evans et al. | |
| 2021/0259856 A1 | 8/2021 | Lince et al. | |
| 2022/0202595 A1 * | 6/2022 | Sun | A61F 2/70 |

FOREIGN PATENT DOCUMENTS

| | | |
|---|---|---|
| CN | 102462533 B | 3/2014 |
| CN | 103536426 B | 7/2014 |
| CN | 204382296 U | 6/2015 |
| CN | 105125381 B | 1/2017 |
| CN | 107116322 A | 9/2017 |
| CN | 208319499 U | 1/2019 |
| CN | 111437081 A | 7/2020 |
| CN | 110074905 B | 10/2020 |
| CN | 112571403 A | 3/2021 |
| CN | 216127254 U | 3/2022 |
| EP | 3749258 A1 | 12/2020 |
| JP | 2016067636 A | 5/2016 |
| SU | 1123684 A1 | 11/1984 |
| WO | WO 2012/098347 | 7/2012 |
| WO | WO 2019/156643 | 8/2019 |
| WO | WO 2020/164886 | 8/2020 |

OTHER PUBLICATIONS

Albers et al., UpperBody of a new Humanoid Robot—the Design of Armar III. Humanoids '06. IEEE 2006. 308-313.
Asfour et al., ARMAR-4: A 63 DOF Torque Controlled Humanoid Robot. 2013 13th IEEE-RAS International Conference on Humanoid Robots (Humanoids). Oct. 15-17, 2013. Atlanta, GA. 7 pages.
Bai et al., A review of sphericalmotion generation using either spherical parallel manipulators or spherical motors. Mechanism and Machine Theory. 2019, 140, 377-388.
Bajaj et al., Design and Preliminary Evaluation of a 3-DOF Powered Prosthetic Wrist Device. 2018 7th IEEE International Conference on Biomedical Robotics and Biomechatronics (Biorob), Enschede, The Netherlands, Aug. 26-29, 2018. 1-7.
Bajaj et al., State of the Art in Artificial Wrists: A Review of Prosthetic and Robotic Wrist Design. IEEE Transactions on Robotics, vol. 35, No. 1, Feb. 2019. 261-277.
Bandara et al., A multi-DoF Anthropomorphic Transradial Prosthetic Arm. 2014 5th IEEE RAS & EMBS Internaitonal Conference on Biomedical Robotics and Biomechatronics. Downloaded Sep. 17, 2021. 1039-1044.
Bridgwater et al., The Robonaut 2 Hand—Designed to Do Work With Tools. 2012 IEEE International Conference on Robotics and Automation. RiverCentre, Saint Pau, Minnesota, USA. May 14-18, 2012. 6 pages.
Controzzi et al., Bio-Inspired Mechanical Design of a Tendon-Driven Dexterous Prosthetic Hand. 32nd Annual International Conference of the IEEE EMBS. Buenos Aires, Argentina, Aug. 31-Sep. 4, 2010. 4 pages.

Damerla et al., Design and Testing of a Novel, High-Performance Two DoF Prosthetic Wrist. IEEE Transactions on Medical Robotics and Bionics, May 2022, vol. 4, No. 2, pp. 502-519.
Dange. Design of a working model of an upper limb prosthesis: Wrist mechanism. New Brunswick, New Jersey. Oct. 2017. 1-66.
Davidson. Development of a Novel Prosthetic Wrist Device, Incorporating the Dart Thrower's Motion. Graduate school of the University of Colorado Thesis. 2017, 1-149.
Fite et al., A Gas-Actuated Anthropomorphic Prosthesis for Transhumeral Amputees. IEEE Transactions on Robotics, Feb. 2008, vol. 24, No. 1, 159-169.
Grebenstein et al., The DLR Hand Arm System. 2011 IEEE International Conference on Robotics and Automation. Shanghai International Conference Center. May 9-13, 2011, Shanghai, China. 8 pages.
Hioki et al., Design and Control of Electromyogram Prosthetic Hand with High Grasping Force. Proceedings of the 2011 IEEE. International Conference on Robotics and Biomimetics. Dec. 7-11, 2011, Phuket, Thailand. 1-6.
Johannes et al., The Modular Prosthetic Limb. Wearable Robotics. Elsevier Inc. 2020. 393-444.
Kaminaga et al., Mechanism and Control of Whole-Body Electro-Hydrostatic Actuator Driven Humanoid Robot Hydra. 2016 International Symposium on Experimental Robotics. pp. 656-665.
Kim et al., A Bioinspired Lightweight Wrist for High-DoF Robotic Prosthetic Arms. IEEE/ASME Transactions on Mechatronics, vol. 24, No. 6, Dec. 2019. 10 pages.
Kim et al., Quaternion Joint: Dexterous 3-DOF Joint Representing Quaternion Motion fo rHigh-Speed Safe Interaction. 2018 IEEE/RSJ International Conference on Intelligent Robots and Systems (IROS) Madrid, Spain, Oct. 1-5, 2018. 8 pages.
Kim et al., RoboRay Hand: A Highly Backdrivable Robotic Hand with Sensorless Contact Force Measurements. 2014 IEEE International Conference on Robotics & Automation (ICRA) Hong Kong convention and Exhibitin Center, May 31-Jun. 7, 2014. Hong Kong, China. 7 pages.
Kundu et al., Development of a 5 DOF Prosthetic Arm for Above Elbow Amputees. Proceedings of 2008 IEEE Internaitonal Conference on Mechatronics and Automation. IEEE, 2008, 207-212.
Kyberd et al., Two-degree-of-freedom powered prosthetic wrist. JRRD. 2011, 48(6), 609-618.
Leal-Naranjo et al., Design and kinematic analysis of a new 3-dof spherical parallel manipulator for a prosthetic wrist. Journal of the Brazilian Society of Mechanical Sciences and Engineering. 2020; 42:63. 1-12.
Lee et al., A Humanoid Robotic Wrist With Two-Dimensional Series Elastic Actuation for Accurate Force/Torque Interaction. IEEE/ASME Transactions on Mechatronics. 2016, 1-10.
Lee et al., Design of a Wearable 3-DOF Forearm Exoskeleton for Rehabilitation and Assistive Purposes. Proceedings of the ASME 2017 International Mechanical Engineering Congress and Exposition. IMECE2017. Nov. 3-9, 2017, Tampa Florida, USA. 10 pages.
Lee et al., Tendon-Driven Compliant Prosthetic Wrist Consisting of Three Rows Based on the Concept of Tensegrity Structure. IEEE Robotics and Automation Letters, Apr. 2021, vol. 6, No. 2, 3956-3963.
Lenzi et al., The RIC Arm-A Small Anthropomorphic Transhumeral Prosthesis. IEEE/ASME Transactions on Mechatronics, Dec. 2016, vol. 21, No. 6, 2660-2671.
Mahmoud et al., An Assistive Tele-Operated Anthropomorphic Robot Hand: Osaka City University Hand II. HIR '11: Proceedings of the 6th international conference on Human-robot interaction. Mar. 2011. 85-92.
Mahmoud et al., Dexterous Mechanism Design for an Anthropomorphic Artificial Hand: Osaka City University Hand I. 2010 IEEE-RAS International Conference on Humanoid Robots. Nashville, TN, USA Dec. 6-8, 2010. 1-6.
Mobius Bionics. Luke Arm System. Datasheet. Retrieved Nov. 10, 2022. 2 pages.
Motion Control Division of Fillauer. MC Standard and ProWrist Rotators, Fact Sheet. Motion Control, Inc. 2019. 2 pages.
Motion Control. Motion Control Powered Flexion Wrist. Motion Control, Inc. 2020. 2 pages.

(56) References Cited

OTHER PUBLICATIONS

Mustafa et al., Development of a Bio-Inspired Wrist Prosthesis. RAM, IEEE 2006. 1-6.

Narvaez et al., Design of a 3-DOF prosthetic wrist for low-cost transradial myoelectric upper limb prosthesis. Chilecon 2019, Oct. 29-31, Valparaiso, Chile. 1-5.

Olsen et al., An Adaptable Prosthetic Wrist Reduces Subjective Workload. bioRxiv 10.1101/808634. Oct. 17, 2019. 20 pages.

Ossur. i-Limb Wrist, Technical Manual. www.ossur.com. Ossur hf. 2019. 291 pages.

Ottobock. Product Information. Otto Bock Healthcare Products GmbH, Dec. 21, 2020. 48 pages.

Patel et al., Parallel Manipulators Applications—A Survey. Modern Mechanical Engineering, 2012, 2, 57-64.

Pons et al., The MANUS-HAND Dextrous Robotics Upper Limb Prothesis: Mechanical and Manipulaiton Aspects. Autonomous Robots, 2004, 16, 143-163.

Razak et al., Development and performance of a new prosthesis system using ultrasonic sensor for wrist movements: a preliminary study. Biomedical Engineering Online, 2014, 13:49. 1-14.

Resnik et al., The DEKA Arm: Its features, functionality, and evolution during the Veterans Affairs Study to optimize the DEKA Arm. Prosthetics and Orthotics International, 2014, vol. 38(6), 492-504.

Roose. Two-Degree-Of-Fredom Pneumatically Powered Wrist Prosthesis. Delft University of Technology. 2014, 1-35.

Song et al., Development of Low-Inertia High-Stiffness Manipulator LIMS2 for High-Speed Manipulaiton of Foldable Objects. 2018 IEEE/RSJ International Conference on Intelligent Robots and Systems (IROS) Madrid, Spain, Oct. 1-5, 2018. pp. 1-7.

Su et al., Design of a Lightweight Forearm Exoskeleton for Fine-Motion Rehabilitation. Conference: 2018 IEEE/ASME International Conference on Advanced Intelligent Mechatronics (AIM). 7 pages.

Sui et al., Mechanism design of a novel two degree-of-freedom ankle rehabilitation robot. iCREATe '10: Proceedings of the 4th International Convention on Rehabilitation Engineering & Assistive Technology. Jul. 2010, Article No. 19, pp. 1-4.

Takeda et al., Development of Prosthetic Arm with Pneumatic Prosthetic Hand and Tendon-Driven Wrist. 31st Annual International Conference of the IEEE EMBS. Minneapolis, Minnesota, USA, Sep. 2-6, 2009. 1-4.

Verleg. Wrist Prosthesis. New Two Degrees-Of-Freedom Hydraulic Wrist Mechanism for Hand Prostheses. Delft University of Technology, Dec. 18, 2015. 70 pages.

Wu et al., A 5-Degrees-of-Freedom Lightweight Elbow-Wrist Exoskeleton for Forearm Fine-Motion Rehabilitation. Oct. 2019. IEEE/ASME Transactions on Mechatronics. pp. 99):1-11.

Yoon et al., The improved DLR Wrist: Design and Analysis of 2-Degrees-of-Freedom Roational Mechanism Using Spatial Antiparallelogram Linkages. Journal of Mechanical Design. May 2021, vol. 143. 12 pages.

Zinck et al., Design of a compact, reconfigurable, prosthetic wrist. Applied Bionics and Biomechanics. 2012, 9, 117-124.

* cited by examiner

Slider Crank 1

60 mm/s

θ

7200 rpm

Slider Crank 2

60 mm/s

θ+110°

7200 rpm

FIG. 10

ROBOTIC PRONATOR

RELATED APPLICATIONS

This application claims priority to and the benefit of U.S. Provisional Patent Application No. 63/430,785, filed on Dec. 7, 2022, which is incorporated herein by reference in its entirety for all purposes.

BACKGROUND

An upper limb prosthesis is an artificial device that serves as a substitute for a partially or entirely lost hand or arm due to an accident, injury, illness, trauma, or congenital defect. The goal of any prosthesis is to provide the user with the ability to perform activities of daily living to regain independence. However, existing designs do not meet all user needs, including, but not limited to, total weight, dexterity, speed, strength, and functionality.

SUMMARY

The Summary is provided to introduce a selection of concepts that are further described below in the Detailed Description. This Summary is not intended to identify key or essential features of the claimed subject matter, nor is it intended to be used as an aid in limiting the scope of the claimed subject matter.

One aspect of the present disclosure provides an assembly comprising: a frame; a motor coupled to the frame and movable with respect to the frame about a pivot axis; a screw rotationally driven by the motor; a nut coupled to the screw and configured to translate along the screw in response to rotation of the screw; and a crank configured to rotate about an output axis. The nut is coupled to the crank and configured to drive the crank about the output axis.

In some embodiments, the assembly further includes a carriage positioned between the nut and the crank, wherein the carriage translates along the screw with the nut.

In some embodiments, the carriage is coupled to the crank at an attachment positioned a distance from the output axis.

In some embodiments, the carriage is configured to rotate relative to the crank about a carriage axis.

In some embodiments, the assembly further includes a linear guide rod coupled to the motor. The linear guide rod is positioned spaced from and parallel to the screw.

In some embodiments, the assembly further includes an end bracket coupled to the linear guide rod and the screw.

In some embodiments, the assembly further includes a position sensor coupled to the end bracket and configured to detect a rotational position of the screw.

In some embodiments, the motor includes a stator, a rotor, and a housing, wherein the stator and the rotor are at least partially received within the housing and the housing is coupled to the frame to move about the pivot axis.

In some embodiments, the motor includes a stator and the stator is coupled to the frame to move about the pivot axis.

In some embodiments, the crank includes: a first end portion aligned with the output axis; an offset portion spaced from the output axis; a drive portion; and a second end portion aligned with the output axis. The drive portion includes an attachment coupled to the nut.

In some embodiments, the frame is cylindrical shape with a longitudinal axis aligned with the output axis of the crank.

In some embodiments, the frame includes a rim that rotationally supports the crank and a plurality of longitudinal struts that are spaced unevenly around a circumference of the rim.

In some embodiments, the assembly further includes a gearbox positioned between the motor and the screw.

In some embodiments, the gearbox is an active multi-speed gearbox.

One aspect of the present disclosure provides an assembly comprising a crank configured to rotate about an output axis; a first motor configured to rotate a first screw; and a first nut assembly configured to translate along the first screw in response to rotation of the first screw. The first nut assembly is coupled to the crank. The assembly further comprises a second motor configured to rotate a second screw; and a second nut assembly configured to translate along the second screw in response to rotation of the second screw. The second nut assembly is coupled to the crank. Translation of the first nut assembly along the first screw is out of phase with translation of the second nut assembly along the second screw.

In some embodiments, the first nut assembly is coupled to the crank at a first attachment and the second nut assembly is coupled to the crank at a second attachment; wherein the first attachment and the second attachment are spaced a distance away from the output axis.

In some embodiments, an angle about the output axis is defined between the first attachment and the second attachment, and wherein the angle is within a range of 70 degrees to 130 degrees.

In some embodiments, the first nut assembly includes a nut and a carriage, wherein the carriage is rotatably coupled to the crank.

In some embodiments, the first motor moves about a first pivot axis and the second motor moves about a second pivot axis.

In some embodiments, the second pivot axis is colinear with the first pivot axis.

In some embodiments, the first motor moves about the first pivot axis through a first range of motion of 20.5 degrees.

In some embodiments, the second motor moves about the second pivot axis through a second range of motion of 20.5 degrees.

In some embodiments, the first motor pivots out of phase with the second motor.

In some embodiments, the first screw defines a first screw axis and the first screw axis moves with respect to the output axis.

In some embodiments, the first screw defines a first screw axis and the first screw axis is fixed relative to the output axis.

In some embodiments, the first screw defines a first screw axis and the first screw axis intersects the output axis.

In some embodiments, the assembly further includes a link positioned between the nut assembly and the crank.

One aspect of the present disclosure provides a system comprising an active two degree of freedom assembly configured to move with a first degree of freedom and a second degree of freedom. The first degree of freedom is a pitch motion and the second degree of freedom is a yaw motion. The system further includes an active single degree of freedom assembly coupled in series with the active two degree of freedom assembly. The active single degree of freedom assembly is configured to move with a single degree of freedom that is a roll motion. The active two degree of freedom assembly is an active wrist assembly, and the active single degree of freedom assembly is an active pronator assembly. The active wrist assembly and the active pronator assembly are positioned within a robotic or prosthetic forearm.

In some embodiments, the pitch motion is flexion and extension motion with a first range of 150 degrees, the yaw motion is radial and ulnar deviation motion with a second range of 75 degrees, and the roll motion has a third range of 190 degrees.

Other aspects of the disclosure will become apparent by consideration of the detailed description and accompanying drawings.

BRIEF DESCRIPTION OF THE DRAWINGS

The accompanying figures and examples are provided by way of illustration and not by way of limitation. The foregoing aspects and other features of the disclosure are explained in the following description, taken in connection with the accompanying example figures (also "FIG.") relating to one or more embodiments.

FIG. 10 is a graph of torque as a function of crank shaft angle for two slider crank mechanisms offset by 90 degrees.

Figure 1:
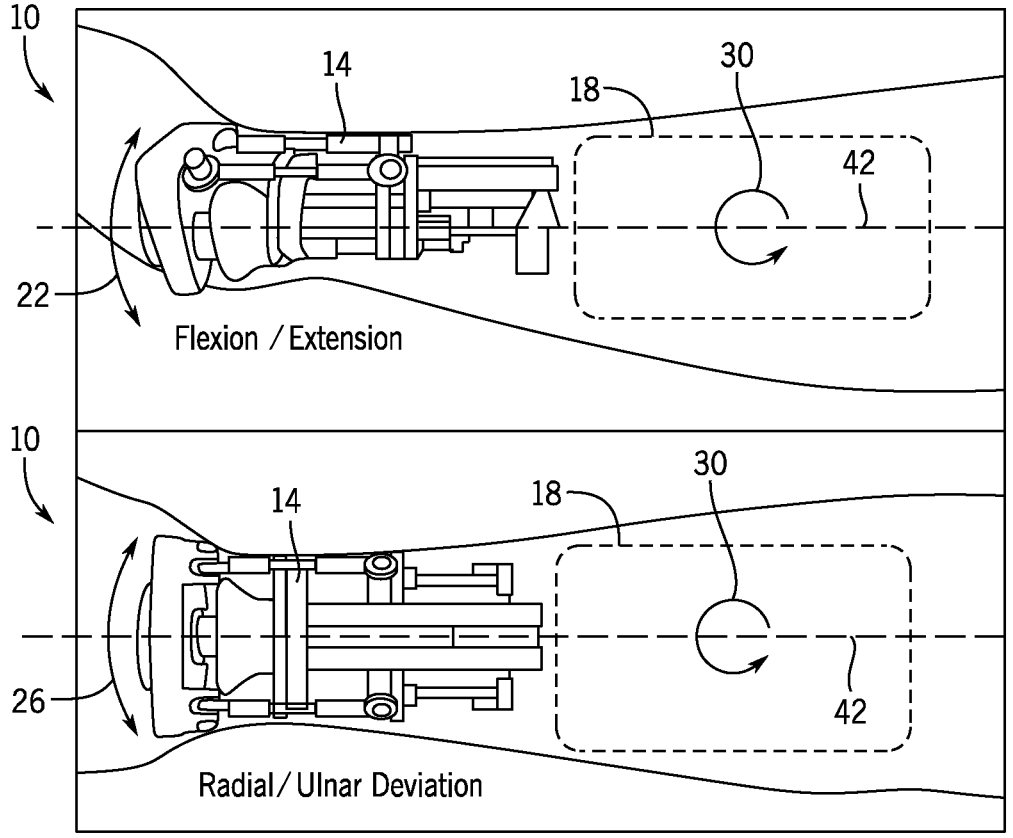
FIG. 1 is a schematic of a wrist system with a two degree of freedom assembly connected in series with a single degree of freedom pronator.

Before any embodiments are explained in detail, it is to be understood that the invention is not limited in its application to the details of construction and the arrangement of components set forth in the following description or illustrated in the following drawings. The invention is capable of other embodiments and of being practiced or of being carried out in various ways.

DETAILED DESCRIPTION

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present disclosure. All publications, patent applications, patents and other references mentioned herein are incorporated by reference in their entirety. The materials, methods, and examples disclosed herein are illustrative only and not intended to be limiting.

For the purposes of promoting an understanding of the principles of the present disclosure, reference will now be made to preferred embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

Articles "a" and "an" are used herein to refer to one or to more than one (i.e., at least one) of the grammatical object of the article. By way of example, "an element" means at least one element and can include more than one element.

"About" and "approximately" is used to provide flexibility to a numerical range endpoint by providing that a given value may be "slightly above" or "slightly below" the endpoint without affecting the desired result.

The use herein of the terms "including," "comprising," or "having," and variations thereof, is meant to encompass the elements listed thereafter and equivalents thereof as well as additional elements. As used herein, "and/or" refers to and encompasses any and all possible combinations of one or more of the associated listed items, as well as the lack of combinations when interpreted in the alternative ("or").

Moreover, the present disclosure also contemplates that in some embodiments, any feature or combination of features set forth herein can be excluded or omitted. To illustrate, if the specification states that an apparatus comprises components A, B, and C, it is specifically intended that any of A, B or C, or a combination thereof, can be omitted and disclaimed singularly or in any combination.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure.

The term "coupled," as used herein, is defined as "connected," although not necessarily directly, and not necessarily mechanically. The term coupled is to be understood to mean physically, magnetically, chemically, electrically, or otherwise coupled, connected or linked and does not exclude the presence of intermediate elements between the coupled elements absent specific contrary language.

Unless otherwise defined, all technical terms used herein have the same meaning as commonly understood by one of ordinary skill in the art to which this disclosure belongs.

With reference to FIG. 1, a prosthetic system 10 is shown with an active two degree of freedom assembly 14 connected in series with an active single degree of freedom assembly 18. The active two degree of freedom assembly 14 is configured to move with a first degree of freedom and a second degree of freedom. In the illustrated embodiment, the first degree of freedom is a pitch motion 22, and the second degree of freedom is a yaw motion 26. The active single degree of freedom assembly 18 is coupled in series with the active two degree of freedom assembly 14, and the active single degree of freedom assembly 18 is configured to move with a single degree of freedom that is a roll motion 30.

In the illustrated embodiment the active two degree of freedom assembly 14 is an active wrist assembly. One example of such a two degree of freedom, active wrist assembly is detailed in R. Damerla et al., "Design and Testing of a Novel. High-Performance Two DoF Prosthetic Wrist," in *IEEE Transactions on Medical Robotics and Bionics*, vol. 4, no. 2, pp. 502-519, May 2022, incorporated herein in its entirety. In the illustrated embodiment, the active single degree of freedom assembly 18 is an active pronator assembly. In the illustrated embodiment, the active wrist assembly 14 and the active pronator assembly 18 are positioned within a robotic or prosthetic forearm. In one embodiment, the pitch motion 22 is flexion and extension motion with a first range of approximately 150 degrees, the yaw motion 26 is radial and ulnar deviation motion with a second range of approximately 75 degrees, and the roll motion 30 has a third range of approximately 190 degrees. In other applications, the active two degree of freedom assembly 14 and the active single degree of freedom assembly 18 are incorporated into a robotic shoulder, hip, angle, or any robotic joint with at least three degrees of freedom. In some embodiments, the rotational axes of rotation for the three degrees of freedom intersect.

Figure 2:
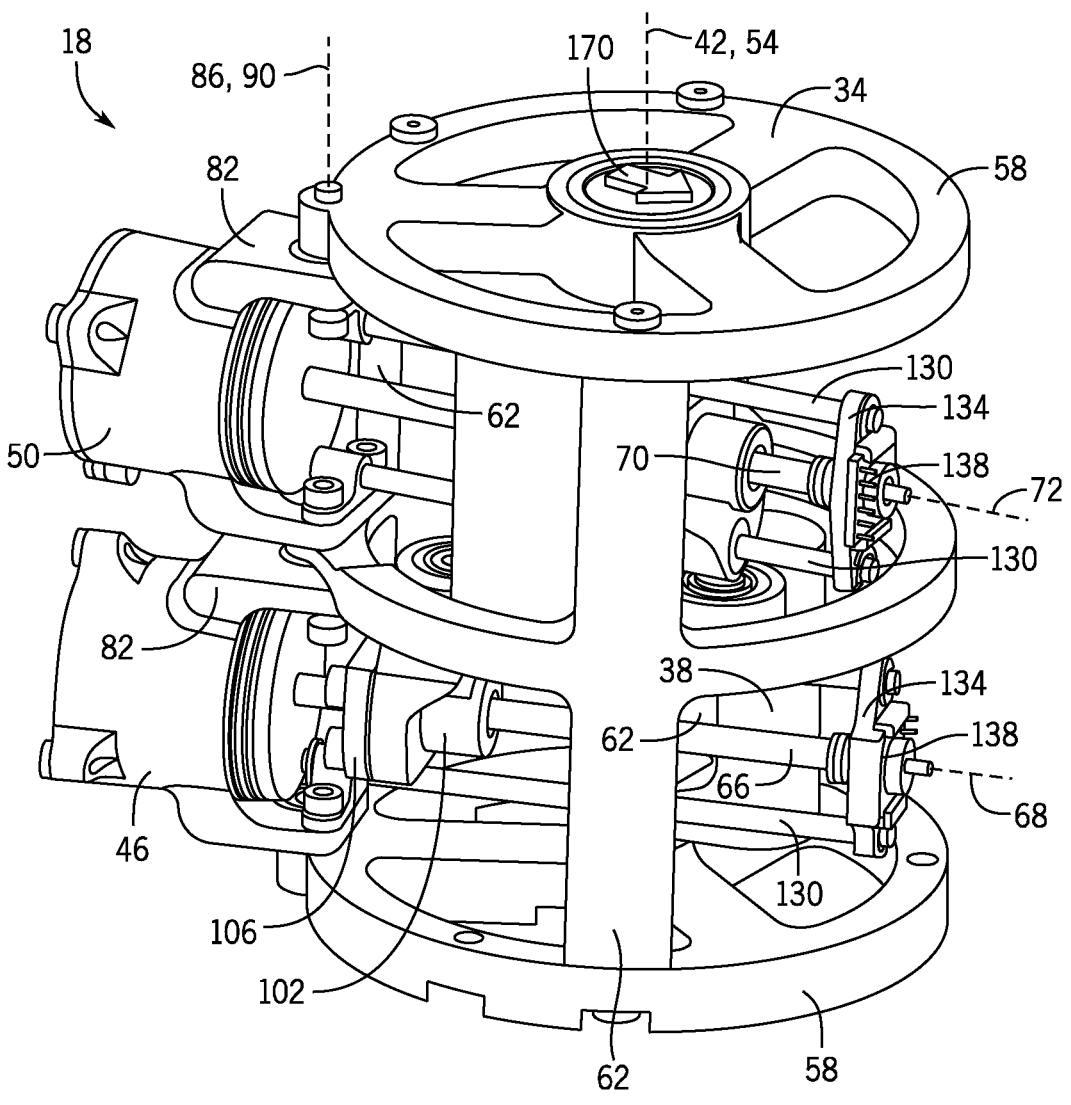
FIG. 2 is a perspective view of a robotic pronator assembly.

With reference to FIG. 2, the active pronator assembly 18 includes a frame 34, a crank 38 configured to rotate about an output axis 42, a first motor 46, and a second motor 50. The frame 34 is cylindrical shape with a longitudinal axis 54 that is aligned with the output axis 42 of the crank 38. In the illustrated embodiment, the frame 34 includes rims 58 that rotationally support the crank 38 and a plurality of longitudinal struts 62 that are spaced unevenly around a circumference of the rims 58. In other words, the struts 62 are not spaced evenly around the frame 34 with respect to the output axis 42 of the crank 38. In some embodiments, the struts are spaced evenly around a circumference of the rims.

Figure 3:
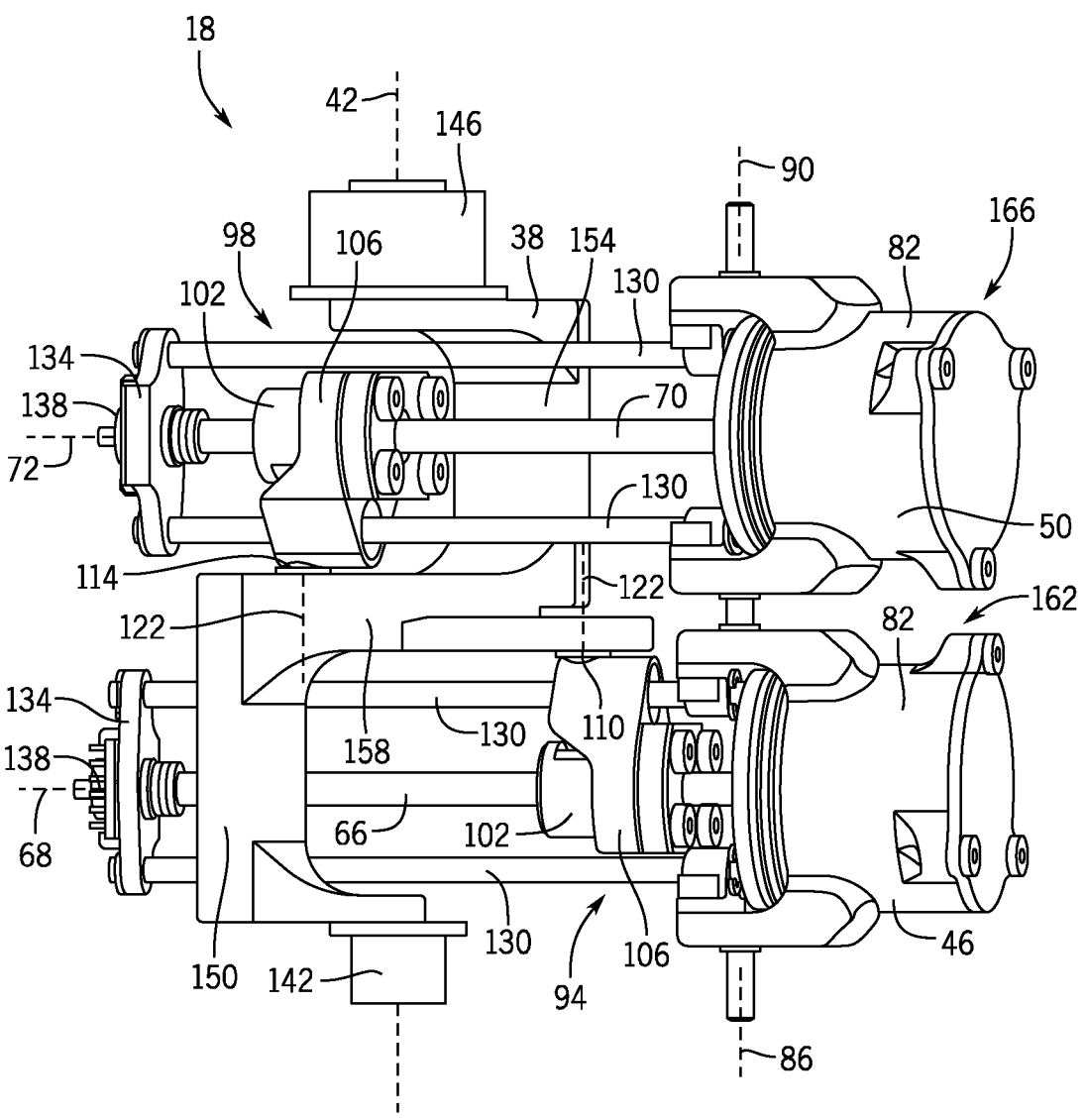
FIG. 3 is a side view of the robotic pronator assembly of FIG. 2, with portions removed for clarity.
Figure 4:
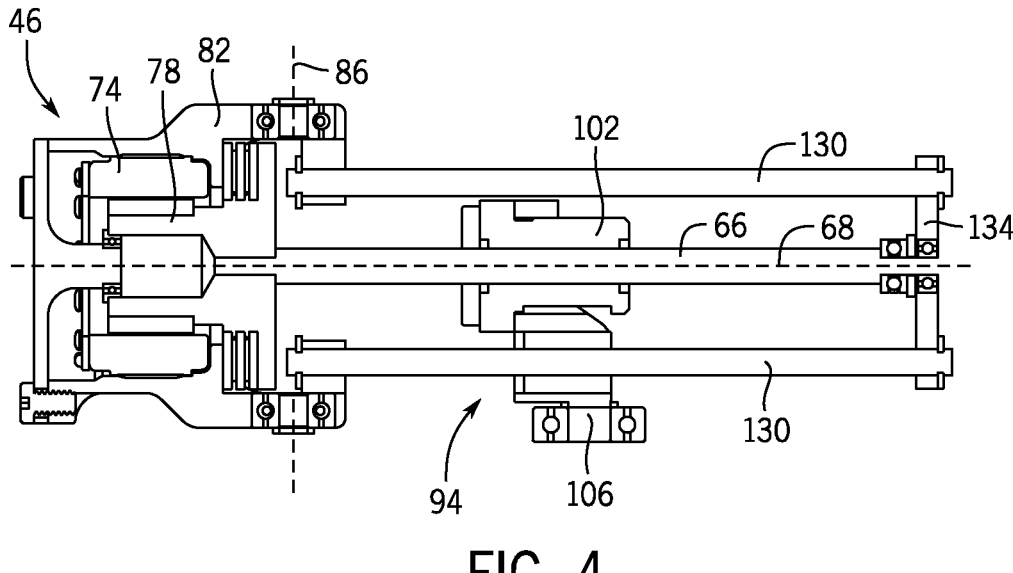
FIG. 4 is a cross-sectional view of a motor, a screw, and a nut assembly of the robotic pronator assembly of FIG. 2.

With reference to FIG. 3, the assembly 18 further includes a first screw 66 rotationally driven by the first motor 46 about a first screw axis 68 and a second screw 70 rotationally driven by the second motor 50 about a second screw axis 72. In other words, the first motor 46 is configured to rotate the first screw 66 and the second motor 50 is configured to rotate the second screw 70. In the illustrated embodiment, the second screw 70 is spaced from and approximately parallel to the first screw 66. In some embodiments, the motors 46, 50 are brushless DC motors. With reference to FIG. 4, in the illustrated embodiment, the motor 46 includes a stator 74, a rotor 78, and a housing 82. In some embodiments, the stator 74 and the rotor 78 are at least partially received within the housing 82. In some embodiments, the motor is coupled with a gearbox (e.g., a planetary gearbox, an active multi-speed gearbox, etc.) and the screw is coupled to the output of the gearbox.

With reference to FIG. 3, the first motor 46 is coupled to the frame 34 and moves about a first pivot axis 86. In other words, the first motor 46 is coupled to the frame 34 and movable with respect to the frame 34 about the first pivot axis 86. Also, the second motor 50 is coupled to the frame 34 and moves about a second pivot axis 90. In the illustrated embodiment, the second pivot axis 90 is colinear with the first pivot axis 86. In some embodiments, the second pivot axis 90 is spaced from and parallel to the first pivot axis 86. In the illustrated embodiment, the motor housing 82 is coupled to the frame 34 and is free to move about the pivot axis 86, 90. In some embodiments, the motor stator acts as the housing and the motor does not includes a separate housing. In which case, the stator is coupled to the frame and is free to move about the pivot axis with respect to the frame.

Figure 7A:
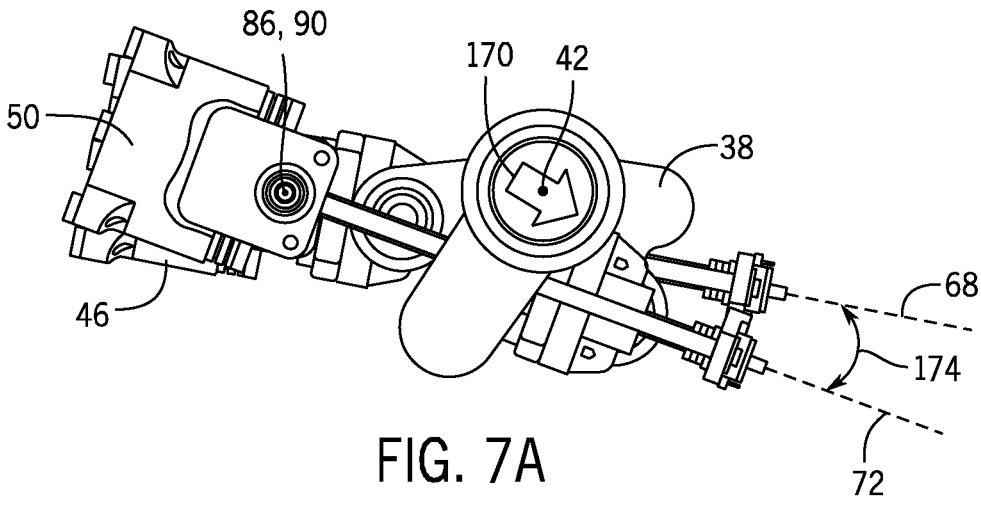
FIG. 7A is a top view of FIG. 6A, with the robotic pronator assembly in the first position.
Figure 7B:
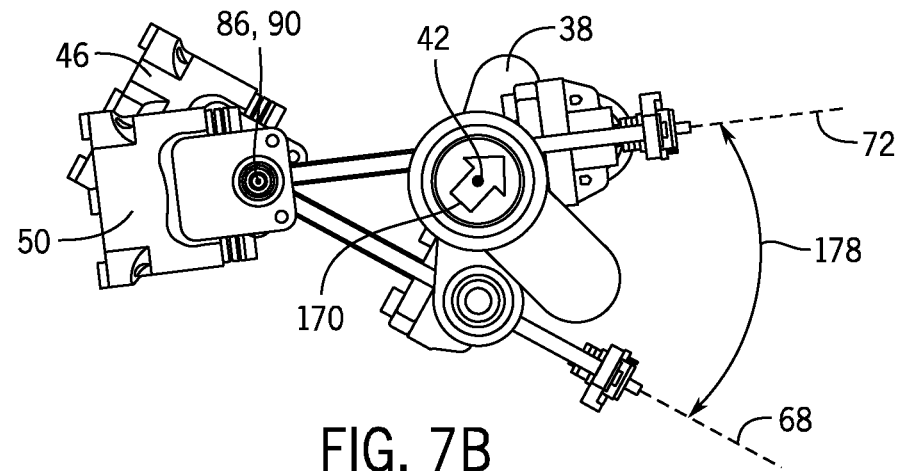
FIG. 7B is a top view of FIG. 6B, with the robotic pronator assembly in the second position.
Figure 7C:
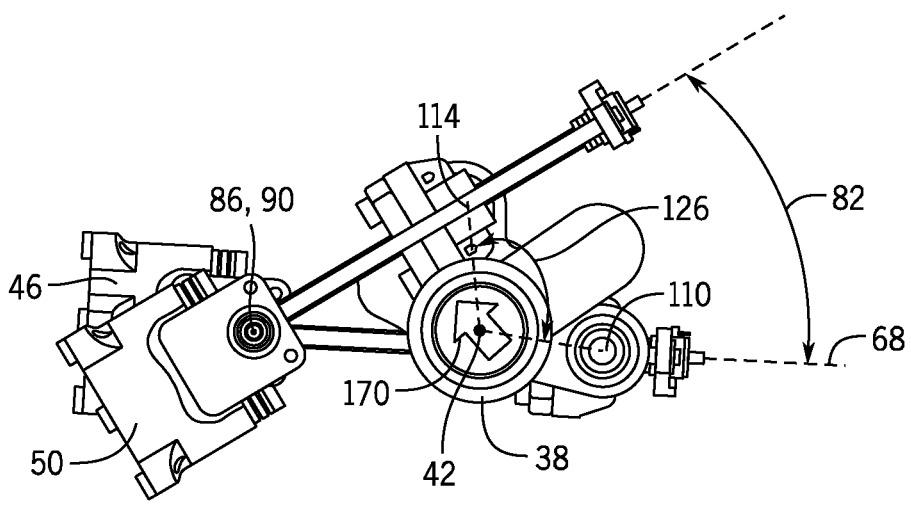
FIG. 7C is a top view of FIG. 6C, with the robotic pronator assembly in the third position.

With reference to FIGS. 7A-7C, the first motor 46 moves about the first pivot axis 86 through a first range of motion and the second motor 50 moves about the second pivot axis 90 through a second range of motion. In some embodiments, the first range of motion is the same as the second range of motion. In the illustrated embodiment, the first motor 46 pivots about the first pivot axis 86 out of phase with the second motor 50 pivoting about the second pivot axis 90.

In some embodiments, the first and/or second range of motion for the motors pivoting is within the range of approximately 0 degrees and approximately 180 degrees. In the illustrated embodiment, the first range of motion for the first motor 46 is approximately 20.5 degrees, and the second range of motion for the second motor 50 is approximately 20.5 degrees. In some embodiments, the first motor 46 rotates approximately 17 degrees about the first pivot axis 86 in one direction and approximately 3.5 degrees about the first pivot axis 86 in the opposite direction.

With reference to FIG. 3, a first nut assembly 94 is configured to translate along the first screw 66 in response to rotation of the first screw 66, and a second nut assembly 98 is configured to translate along the second screw 70 in response to rotation of the second screw 70. The first nut assembly 94 includes a nut 102 coupled to the first screw 66 and a carriage 106 coupled to the crank 38. Likewise, the second nut assembly 98 includes a nut 102 and a carriage 106 rotatably coupled to the crank 38. In the illustrated embodiment, the carriage 106 is rotatably coupled to the crank 38. The nut 102 is configured to translate along the screw 66 in response to rotation of the screw 66. In some embodiments, the screw and nut arrangement is a ball screw or a lead screw configuration.

The first nut assembly 94 is coupled to the crank 38, and the second nut assembly 98 is coupled to the crank 38. Specifically, the nut 102 is coupled to the crank 38 through the carriage 106 and is configured to drive the crank 38 about the output axis 42. The carriage 106 is positioned between the nut 102 and the crank 38, and the carriage 106 translates along the screw 66, 70 with the nut 102. In other words, the carriage 106 co-translates with the nut 102 along the screw 66, 70.

Figure 5:
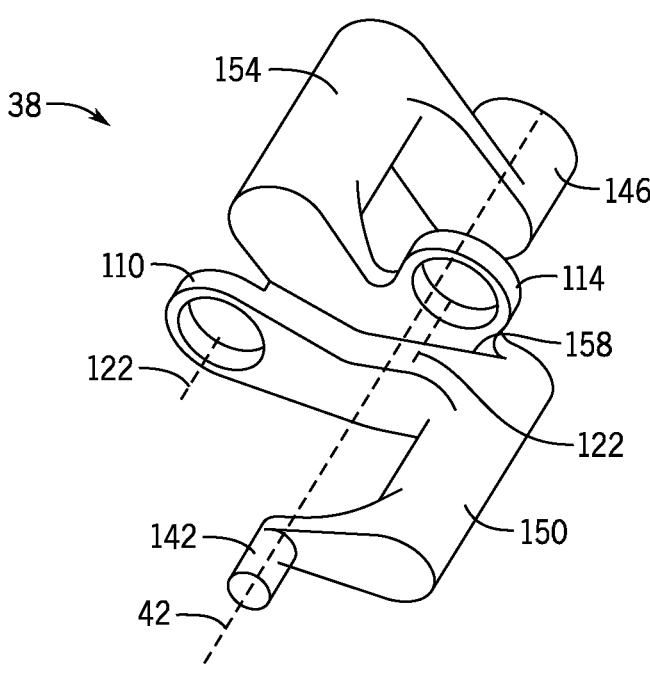
FIG. 5 is a perspective view of a crank of the robotic pronator assembly of FIG. 2.

With continued reference to FIG. 3, as detailed further herein, the first nut assembly 94 and the second nut assembly 98 rotationally drive the crank 38 about the output axis 42. The first nut assembly 94 is coupled to the crank 38 at a first attachment 110, and the second nut assembly 98 is coupled to the crank 38 at a second attachment 114. The first attachment 110 and the second attachment 114 are spaced a distance away from the output axis 42 (FIG. 5). In the illustrated embodiment, the carriages 106 are coupled to the crank 38 at the attachments 110, 114 and the carriages 106 are configured to rotate relative to the crank 38 about a respective carriage axis 122. In the illustrated embodiment, the carriage axis 122 is spaced from and parallel to the pivot axis 86 of the first motor 46, the pivot axis 90 of the second motor 50 and the output axis 42.

An angle 126 (FIG. 7C) about the output axis 42 (e.g., an included angle) is defined between the first attachment 110 and the second attachment 114. In some embodiments, the angle 126 is within a range of approximately 70 degrees to approximately 130 degrees. In some embodiments, the angle 126 is within a range of approximately 0 degrees to approximately 180 degrees. In the illustrated embodiment, the angle 126 is approximately 110 degrees. In some embodiments, the crank attachment points 110, 114 for the nut assemblies 94, 98 move through a range of motion of approximately 160 degrees.

With reference to FIG. 3, the assembly 18 further includes linear guide rods 130 coupled to the motors 46, 50. The linear guide rods 130 on the first motor 46 are positioned spaced from and parallel to the first screw 66, and the linear guide rods 130 on the second motor 50 are positioned spaced from and parallel to the second screw 70. An end bracket 134 is coupled to the linear guide rods 130 and the first screw 66, and an end bracket 134 is coupled to the linear guide rods 130 and the second screw 70. In some embodiments, a position sensor 138 is coupled to the end bracket 134 and configured to detect a rotational position of the corresponding screw 66, 70.

With reference to FIG. 5, the crank 38 includes a first end portion 142 aligned with the output axis 42 and a second end portion 146 aligned with the output axis 42, opposite the first end portion 142. The crank 38 further includes a first offset portion 150 spaced from the output axis 42 and a second offset portion 154 spaced from the output axis 42. The offset portions 150, 154 create space in which to receive at least a portion of the screws 66, 70, respectively and the linear guide rods 130. In the illustrated embodiment, the crank 38 includes a drive portion 158 positioned between the first offset portion 150 and the second offset portion 154. The drive portion 158 includes the first attachment 110 that couples to the first nut assembly 94 and the second attachment 114 that couples to the second nut assembly 98. In some embodiments, the crank is only supported on one end, in a cantilevered arrangement.

Together, the first screw 66, the first nut assembly 94 and the crank 38 at least partially form a first slider crank mechanism 162, and the second screw 70, the second nut assembly 98, and the crank 38 at least partially form a second slider crank mechanism 166. In some embodiments, the assembly 18 includes any number of slider crank mechanisms. In some embodiments, the assembly 18 includes a single slider crank mechanism. In some embodiments, the assembly 18 includes at least two slider crank mechanisms. In some embodiments, the assembly 18 includes three or more slider crank mechanisms. In some embodiments, the slider crank mechanisms of the assembly 18 are stacked along the output axis 42. In some embodiments, the slider crank mechanisms are structurally identical but operate out of phase with each other during operation of the assembly 18.

As detailed further herein, translation of the first nut assembly 94 along the first screw 66 is out of phase with translation of the second nut assembly 98 along the second screw 70. In other words, the first slider crank mechanism 162 operates out of phase with the second slider crank mechanism 166. Advantageously, the torque ripple associated with a first slider crank mechanism is smoothed out when combined with the torque of a second slider crank mechanism operating out of phase with the first slider crank mechanism. In other words, the combination of more than one out of phase slider crank mechanism increases and smooths the total output torque.

Figure 6A:
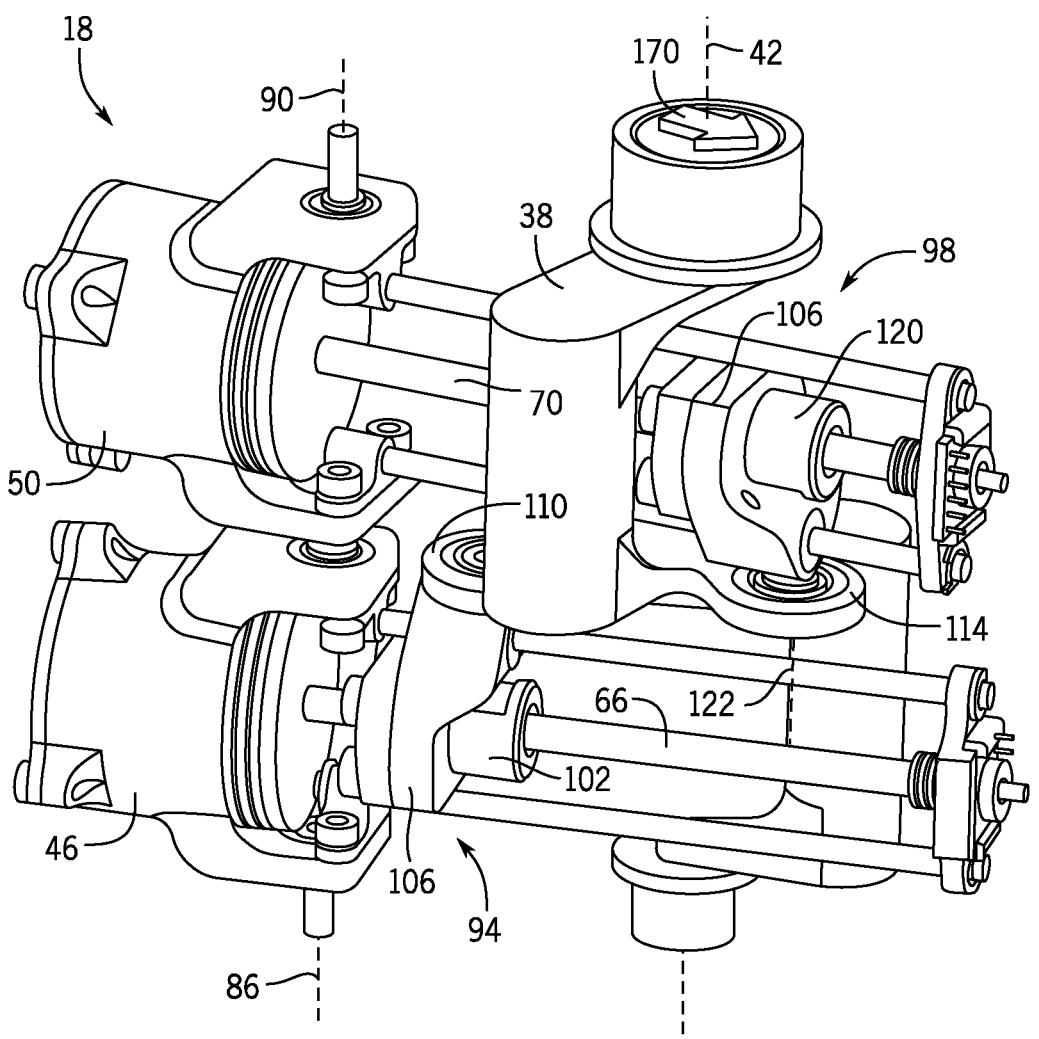
FIG. 6A is a perspective view of the robotic pronator assembly of FIG. 2, with portions removed for clarity, shown in a first position.

Operation of the assembly 18 is illustrated in FIGS. 6A-6C and FIGS. 7A-7C. With reference to FIGS. 6A and

7A, the assembly 18 is in a first position. An arrow 170 on the second end portion 146 of the crank 38 illustrates the crank 38 orientation with respect to the output axis 42. In the first position, an angle 174 (FIG. 7A) defined between the first screw 66 and the second screw 70 is approximately 10 degrees.

Figure 6B:
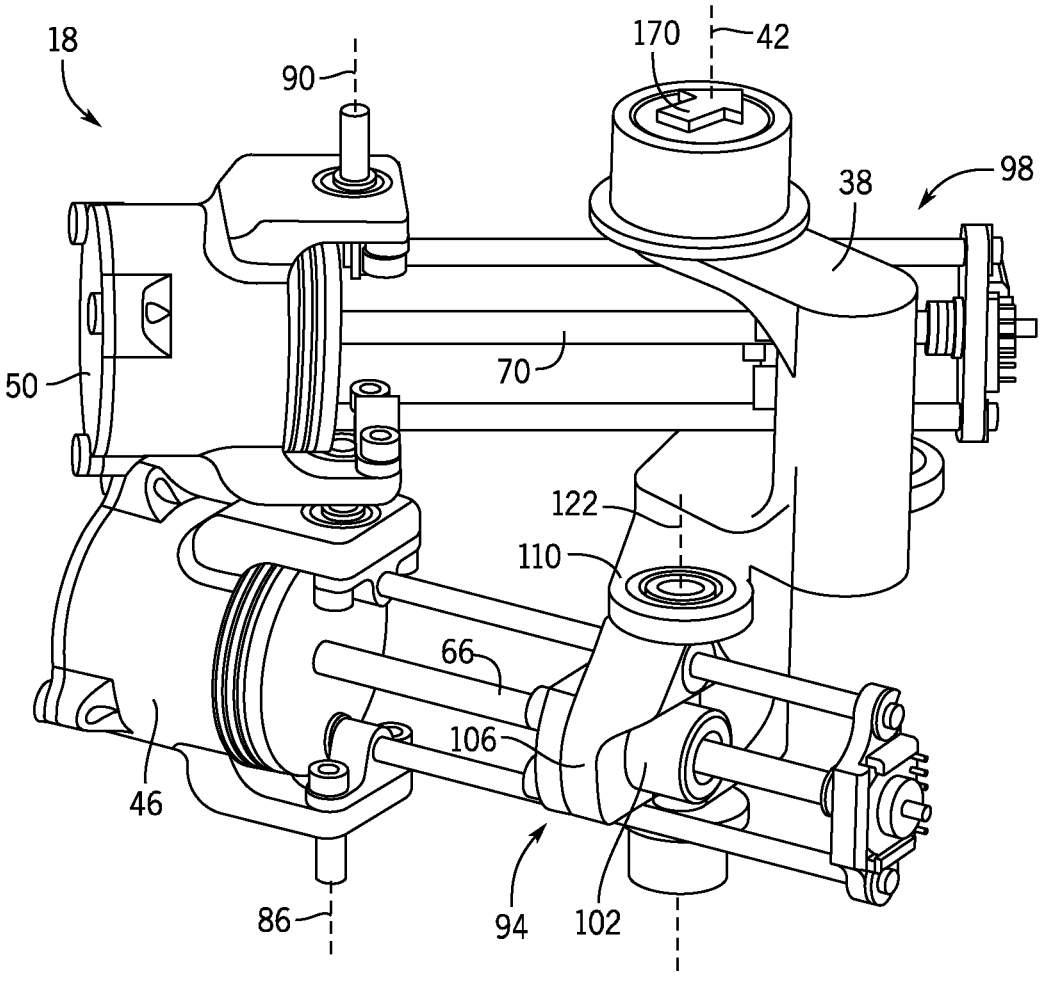
FIG. 6B is a perspective view of the robotic pronator assembly of FIG. 2, with portions removed for clarity, shown in a second position.

With reference to FIGS. 6B and 7B, the assembly 18 is in a second position. The crank 38 is rotated by the nut assemblies 94, 98 and the crank 38 rotates approximately 80 degrees when moving from the illustrated first position to the second position. In the second position, an angle 178 (FIG. 7B) defined between the first screw 66 and the second screw 70 is approximately 35 degrees.

Figure 6C:
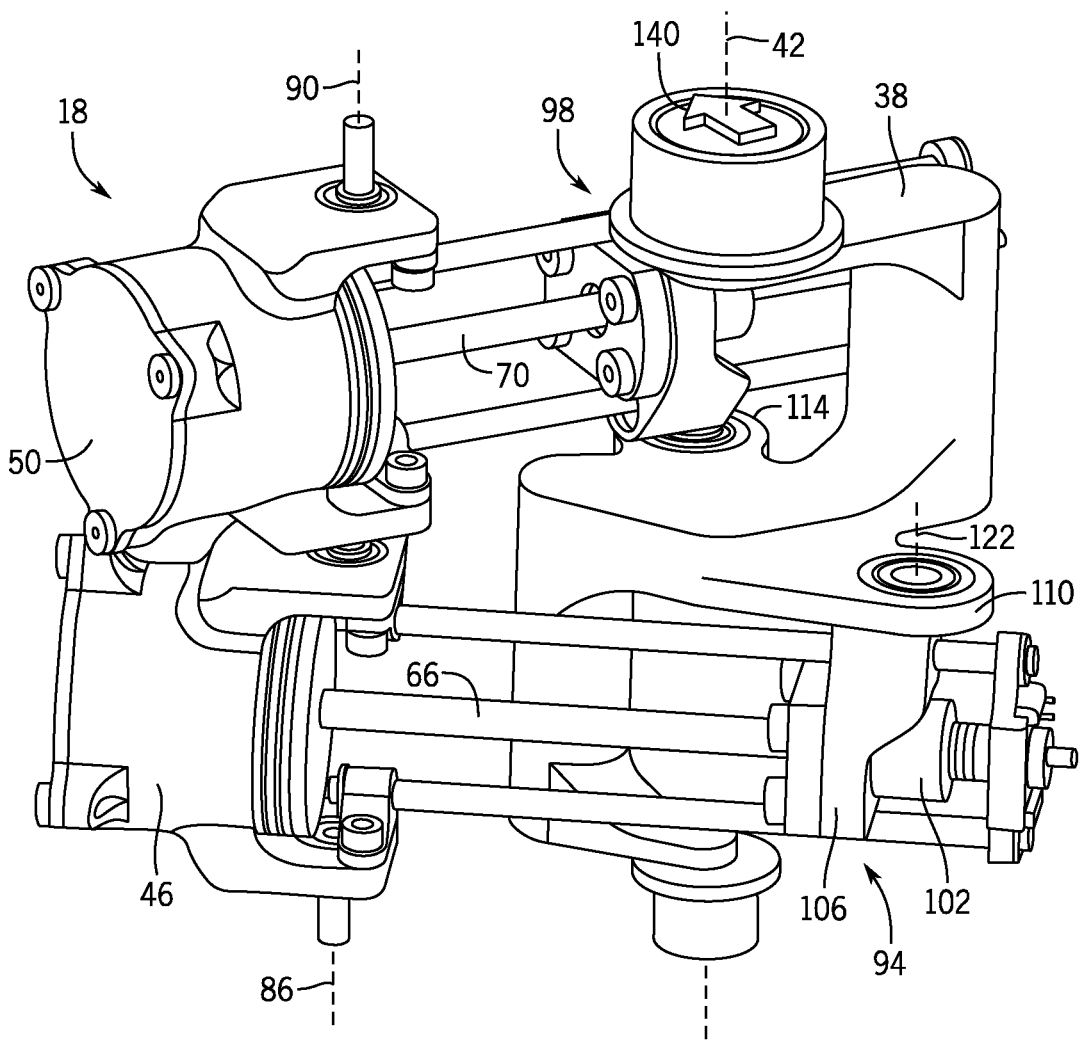
FIG. 6C is a perspective view of the robotic pronator assembly of FIG. 2, with portions removed for clarity, shown in a third position.

With reference to FIGS. 6C and 7C, the assembly 18 is in a third position. The output crank 38 is rotated further by the nut assemblies 94, 98, and the crank 38 rotates approximately 80 degrees when moving from the illustrated second position to the third portion. In the third position, an angle 182 (FIG. 7C) defined between the first screw 66 and the second screw 70 is approximately 35 degrees. In the illustrated embodiment, the relative orientation of the motors 46, 50 and screws 66, 70 varies during operation of the assembly 18.

In some embodiments, the slider crank mechanism is a "standard" slider crank mechanism. In some embodiments, the screw defines a screw axis that is fixed relative to the output axis 42. In some embodiments the screw defines a screw axis that intersects the output axis 42. In some embodiments, an additional link is positioned between the nut assemblies 94, 98 and the crank 38 such that the nut assemblies 94, 98 rotates the crank 38 through the link.

In some embodiments, the slider crank mechanism is an "inverted" slider crank mechanism, including any one of the four kinematic inversions. In some embodiments, the screw defines a screw axis that moves with respect to the output axis 42.

Figure 8A:
FIG. 8A is a schematic of two slider crank mechanisms.
Figure 8A:
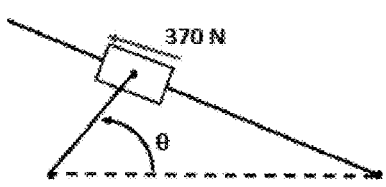
Figure 8A:
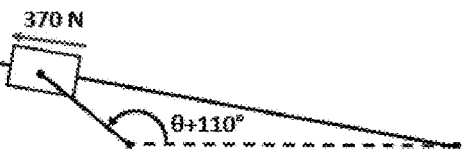
Figure 8B:
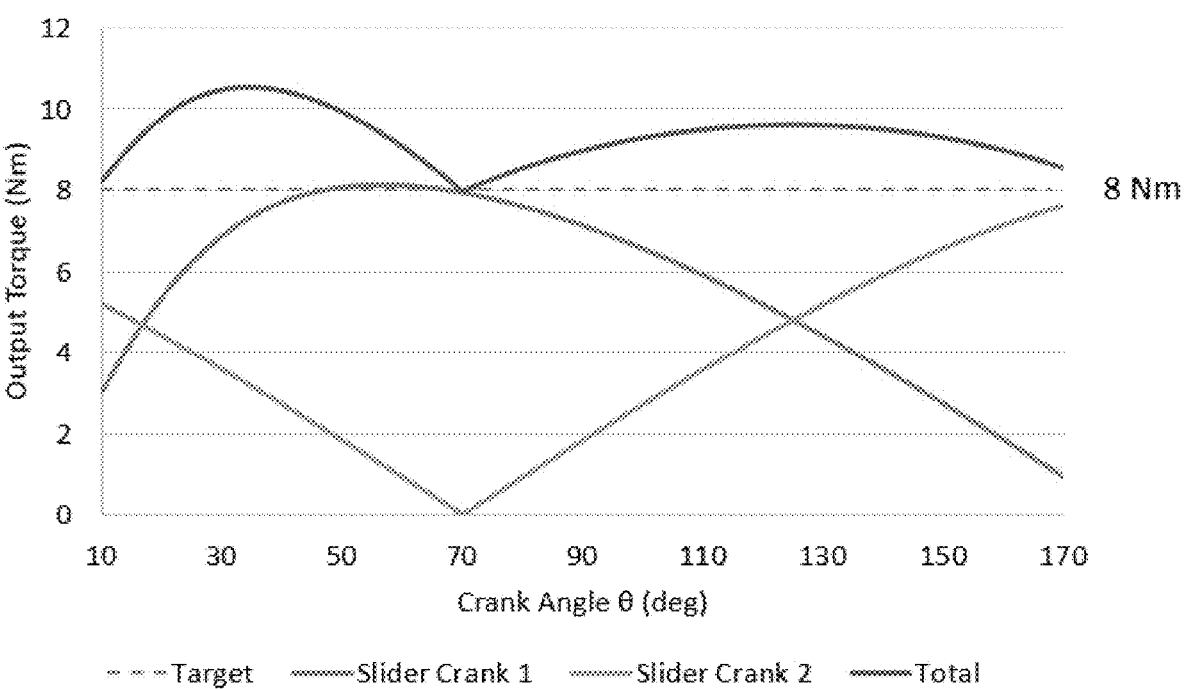
FIG. 8B is a graph of output torque as a function of crank angle for the two slider crank mechanisms of FIG. 8A.

With reference to FIG. 8A, two slider crank mechanisms are illustrated offset from each other. FIG. 8B illustrates the corresponding output torque for the two slider crank mechanisms of FIG. 8A as a function of the crank angle. As shown, the total output torque of the two slider crank mechanisms combined remains above the target threshold torque.

Figure 9A:
FIG. 9A is a schematic of two slider crank mechanisms.
Figure 9A:
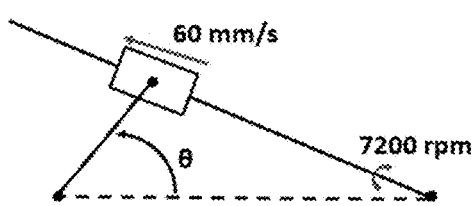
Figure 9B:
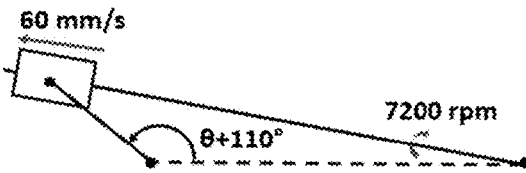
FIG. 9B is a graph of output speed as a function of crank angle for the two slider crank mechanisms of FIG. 9A.
Figure 9B:
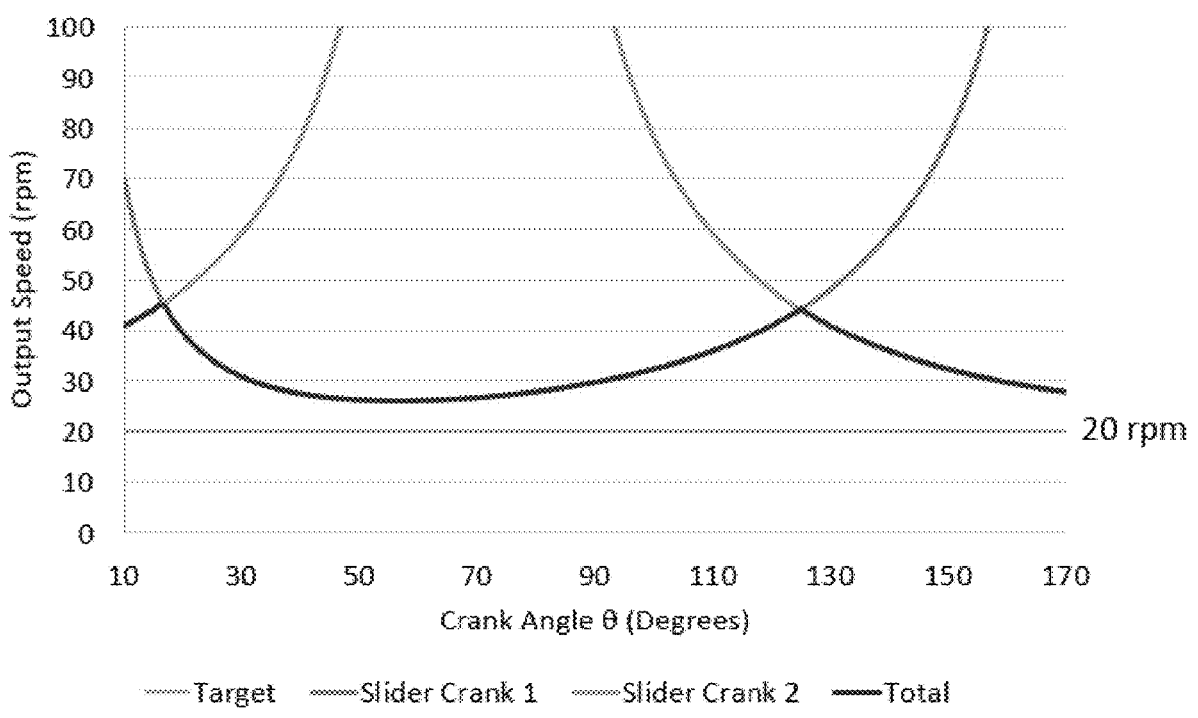

With reference to FIG. 9A, two slider crank mechanisms are illustrated offset from each other but include screws rotationally driven at the same speed (e.g., 7200 rpm). FIG. 9B illustrates the corresponding output speed for the two slider crank mechanisms of FIG. 9A as a function of the crank angle. In the illustrated arrangement, the slower of the two slider crank mechanisms control the output speed at any given crank angle. As shown, the output speed remains above the target threshold speed.

Figure 10:
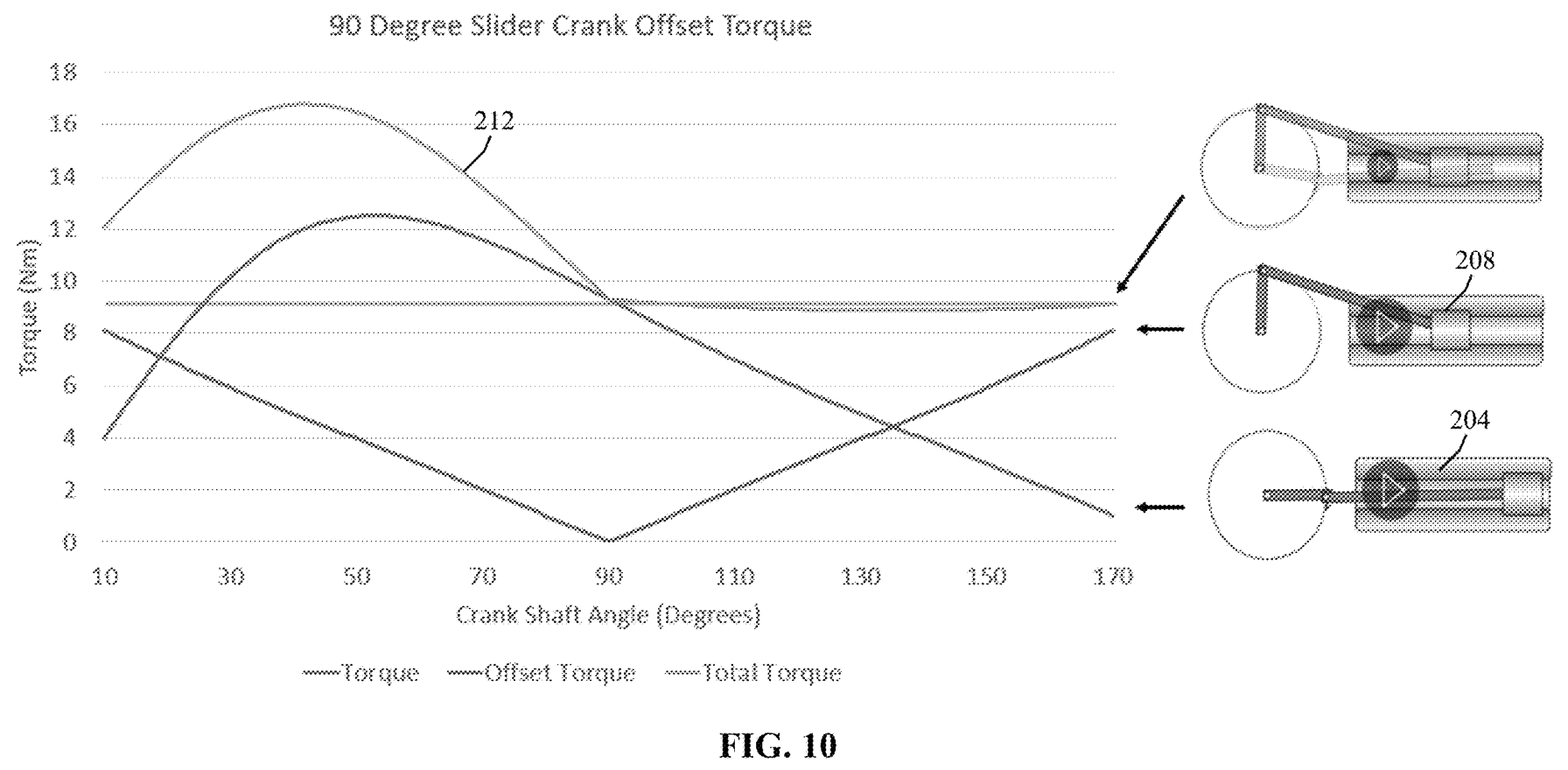
Figure 11:
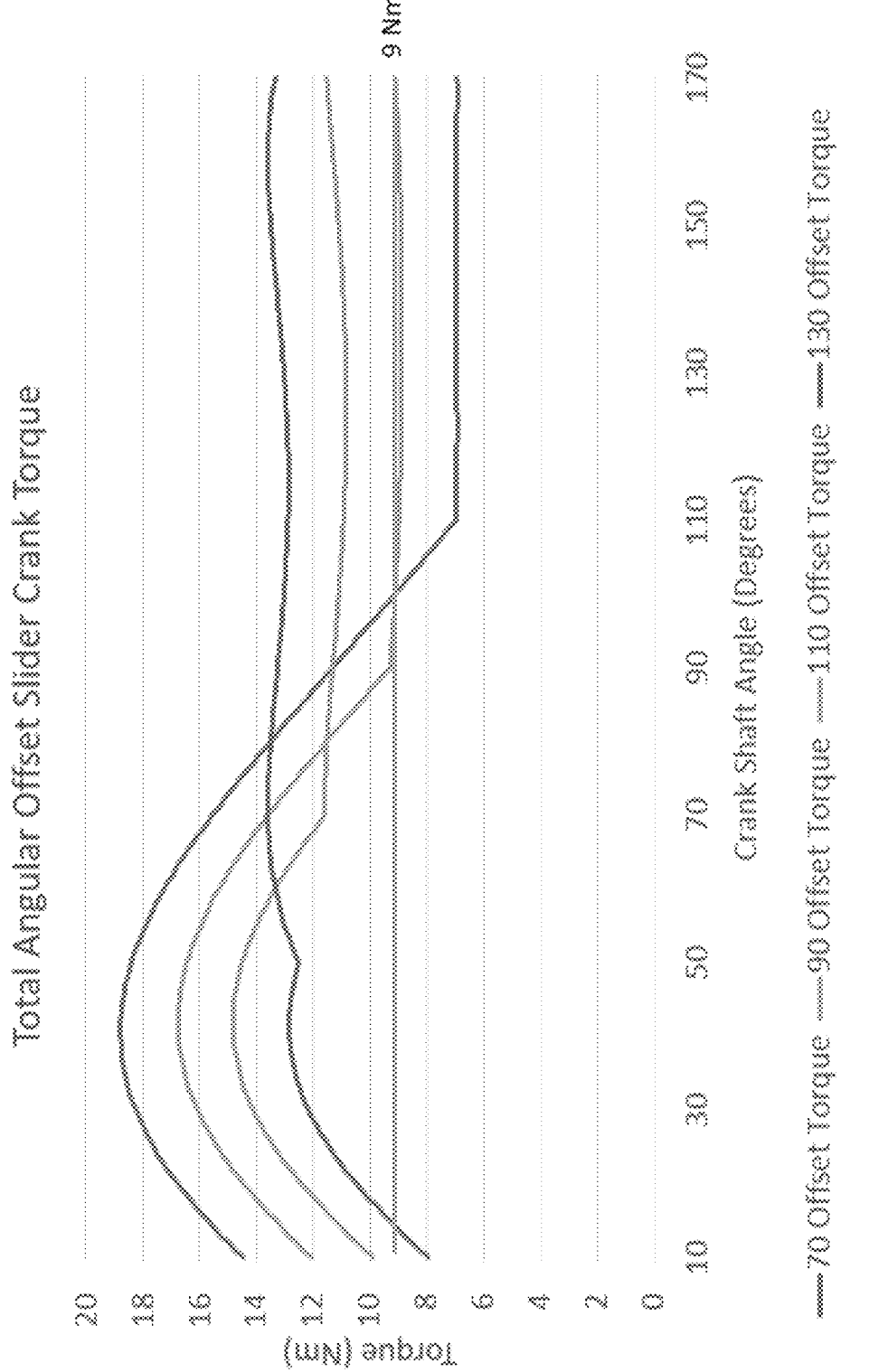
FIG. 11 is a graph of total torque as a function of crank shaft angle for two-slider crank mechanisms offset by 70 degrees, 90 degrees, 110 degrees, and 130 degrees.

With reference to FIG. 10, torque from a first standard slider crank mechanism 204, and torque from a second standard slider crank mechanism 208 that is 90 degrees offset from the first standard slider crank mechanism 204 combine for a total torque 212. With reference to FIG. 11, the amount of phase or angular offset between the slider crank mechanism shown in FIG. 10 can be varied to produce different resulting total torques. FIG. 11 illustrates a graph of the total torque results for various offsets between two standard slider crank mechanisms.

Figure 12:
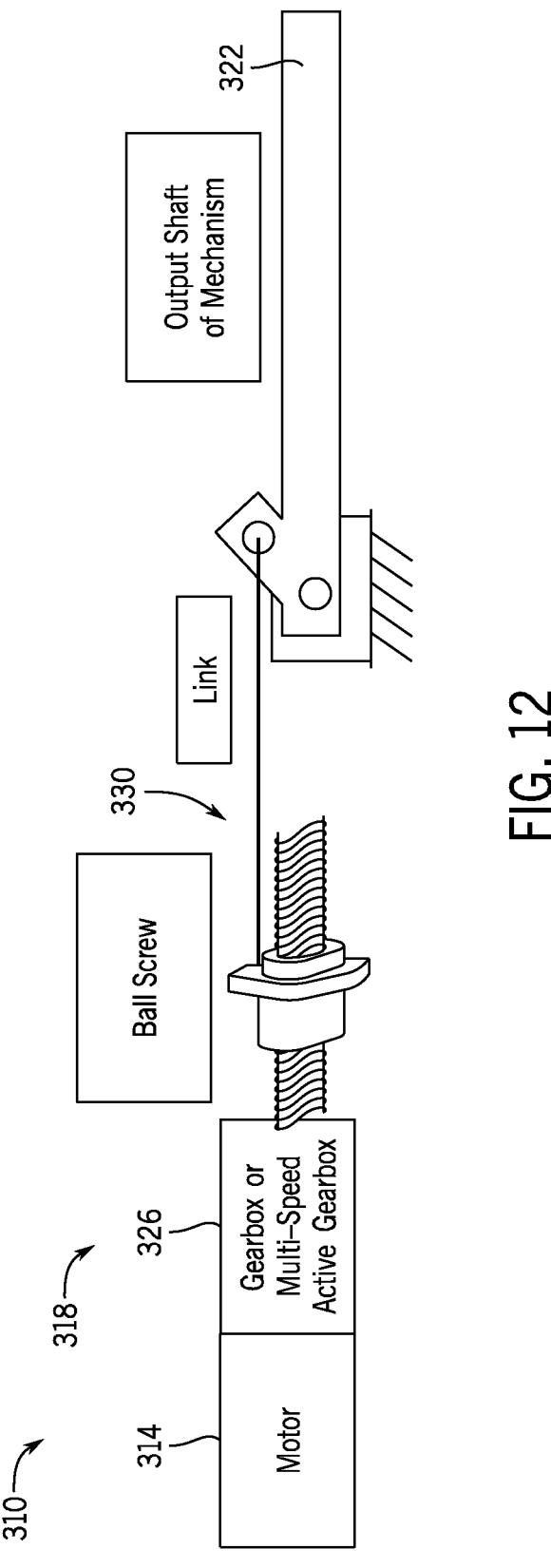
FIG. 12 is a schematic of a prosthetic assembly with a motor, a gearbox, and transmission.

With reference to FIG. 12, a schematic of a robotic assembly 310 is illustrated with a motor 314 (e.g., a rotary actuator), a transmission 318, and an output device 322. In some embodiments, the output device 322 is a finger, a thumb, a hand, a wrist, a forearm, a shoulder, a leg, a humanoid robot, a robotic bird wing, a robotic fish tail, a multi-legged robot (e.g., a dog, a spider), other non-bioinspired robotics, robot-assisted medical devices, or any other suitable prosthetic limb.

In the illustrated embodiment, the transmission 318 includes a gearbox 326 (e.g., a 2-speed active gearbox), and a linkage 330 coupled to the gearbox 326. In the illustrated embodiment, the linkage 330 includes a ball screw and a cable (e.g., a link). In other embodiments, the linkage 330 includes a ball screw, a lead screw, a cable, a four-bar linkage, a six-bar linkage, a multi-bar linkage, an additional gear set, any suitable transmission component, or any combination thereof. The transmission 318 couples the motor 314 output to the finger 322. In the illustrated embodiment, the gearbox 326 is positioned between the motor 314 and the screw. In some embodiments, the gearbox 326 is an active multi-speed gearbox that is movable between a first configuration where the gearbox 326 has a first gear ratio of N:1, where N is not equal to 1, and a second configuration where the gearbox 326 has a gear ratio of 1:1.

The pronator assembly 18 described herein can be used to provide a single degree of freedom rotation that occurs along the length of a limb or other structure (e.g., a forearm) and can be serially connected with other mechanisms (e.g., assembly 14) to create multiple degrees of freedom joints that fit into a specific shape (e.g., a prosthetic hand, shoulder, hip, etc.).

The pronator assembly 18 includes a plurality of slider crank mechanisms 162, 166 that are offset from each other. Together, the plurality of slider crank mechanisms 162, 166 drive a single crank 38. The phase offset between the slider crank mechanisms 162, 166 ensures that at least one of the slider crank mechanisms has a high mechanical advantage at any given crank angle. This enables the pronator assembly 18 to provide a high torque at all crank angles throughout the entire range of motion.

These slider crank mechanisms can be either standard or inverted. Each of the slider crank mechanisms includes a rotary actuator (e.g., a brushless DC motor). In some embodiments, the rotary actuator drives a gearbox such as a planetary gear box or a multi-speed gearbox that can change gear ratios. The output of the motor drives a lead or ball screw and nut. The nut is connected to the crank at a distance from the output axis to generate a torque at all positions except where there is zero mechanical advantage (e.g., toggle positions). A plurality of slider crank mechanisms, each driven by a separate rotary actuator are energized in tandem to ensure they collectively provide the required torque output. In some embodiments, the slider crank mechanisms are stacked one on top of the other.

Using a kinematic inversion of the slider crank mechanism, rather than a standard slider crank, is beneficial for the pronator assembly 18 because it increases the amount of torque that can be produced by the pronator assembly 18 given packaging constraints (e.g., within a forearm). In the illustrated embodiments, two main constraints are (A) the need to package components within a cylindrical volume of 80 mm and (B) the need to provide torque output on an axis that is concentric with this cylindrical volume (see FIG. 1). A standard slider crank has an output crank length of 15 mm when subject to these constraints while the inverted slider crank has an output crank length of 22 mm. The longer crank length results in a greater torque output for a given input force provided by the ball or lead screw slider. However, it is still possible to package a standard slider crank with a 22 mm crank length within the desired cylindrical volume if the constraint (B) of having a concentric output axis is eliminated.

One skilled in the art will readily appreciate that the present disclosure is well adapted to carry out the objects and obtain the ends and advantages mentioned, as well as those inherent herein. The present disclosure described herein are exemplary embodiments and are not intended as limitations on the scope of the present disclosure. Changes therein and other uses will occur to those skilled in the art which are encompassed within the spirit of the present disclosure as defined by the scope of the claims.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference, unless explicitly indicated otherwise. The present disclosure shall control in the event there are any disparities between any definitions and/or description found in the cited references.

Various features and advantages are set forth in the following claims.

What is claimed is:

1. An assembly comprising:
a frame;
a motor coupled to the frame and movable with respect to the frame about a pivot axis;
a screw rotationally driven by the motor;
a nut coupled to the screw and configured to translate along the screw in response to rotation of the screw; and
a crank configured to rotate relative to the frame about an output axis; wherein the nut is coupled to the crank and configured to drive the crank about the output axis; and
a carriage positioned between the nut and the crank, wherein the carriage translates along the screw with the nut; and wherein the carriage rotates relative to the crank about a carriage axis; and
wherein the motor is movable with respect to the output axis of the crank about the pivot axis.

2. The assembly of claim 1, wherein the carriage is coupled to the crank at an attachment positioned a distance from the output axis.

3. The assembly of claim 1, further comprising a linear guide rod coupled to the motor; wherein the linear guide rod is positioned spaced from and parallel to the screw.

4. The assembly of claim 3, further comprising an end bracket coupled to the linear guide rod and the screw.

5. The assembly of claim 4, further comprising a position sensor coupled to the end bracket and configured to detect a rotational position of the screw.

6. The assembly of claim 1, wherein the motor includes a stator, a rotor, and a housing, wherein the stator and the rotor are at least partially received within the housing and the housing is coupled to the frame to move about the pivot axis; and wherein the rotor rotates about a screw axis of the screw.

7. The assembly of claim 1, wherein the motor includes a stator and the stator is coupled to the frame to move about the pivot axis.

8. The assembly of claim 1, wherein the crank includes:
a first end portion aligned with the output axis;
an offset portion spaced from the output axis;
a drive portion; and
a second end portion aligned with the output axis;

wherein the drive portion includes an attachment coupled to the nut.

9. The assembly of claim 1, wherein the frame is cylindrical shape.

10. The assembly of claim 9, wherein the frame includes a rim that rotationally supports the crank and a plurality of longitudinal struts that are spaced unevenly around a circumference of the rim.

11. The assembly of claim 1, further comprising a gearbox positioned between the motor and the screw.

12. The assembly of claim 1, wherein the motor is a first motor, the screw is a first screw, and the nut and the carriage are part of a first nut assembly, and wherein the assembly further comprises:

a second motor configured to rotate a second screw; and a second nut assembly configured to translate along the second screw in response to rotation of the second screw, the second nut assembly coupled to the crank;

wherein translation of the first nut assembly along the first screw is out of phase with translation of the second nut assembly along the second screw.

13. The assembly of claim 12, wherein the first nut assembly is coupled to the crank at a first attachment and the second nut assembly is coupled to the crank at a second attachment; wherein the first attachment and the second attachment are spaced a distance away from the output axis; wherein an angle about the output axis is defined between the first attachment and the second attachment, and wherein the angle is within a range of 70 degrees to 130 degrees.

14. The assembly of claim 12, wherein the pivot axis is a first pivot axis and the second motor moves about a second pivot axis.

15. The assembly of claim 14, wherein the second pivot axis is colinear with the first pivot axis;

wherein the first motor moves about the first pivot axis through a first range of motion of 20.5 degrees;

wherein the second motor moves about the second pivot axis through a second range of motion of 20.5 degrees; and wherein the first motor pivots out of phase with the second motor.

16. The assembly of claim 12, wherein the first screw defines a first screw axis and the first screw axis moves with respect to the output axis.

17. The assembly of claim 12, wherein the first screw defines a first screw axis and the first screw axis is fixed relative to the output axis.

18. The assembly of claim 12, wherein the first screw defines a first screw axis and the first screw axis intersects the output axis.

19. The assembly of claim 12, further comprising a link positioned between the first nut assembly and the crank.

20. The assembly of claim 1, wherein the carriage axis is spaced from and parallel to the pivot axis.

21. The assembly of claim 20, wherein the carriage axis is spaced from and parallel to the output axis; and wherein the frame defines a longitudinal axis; and wherein the longitudinal axis is coaxial with the output axis.

22. The assembly of claim 1, wherein the carriage axis is spaced from and parallel to the output axis.

23. The assembly of claim 1, wherein the pivot axis and the output axis are spaced apart and parallel.

24. The assembly of claim 1, wherein the frame is fixed relative to the output axis of the crank.

25. The assembly of claim 1, wherein the motor rotationally drives the screw about a screw axis; and wherein the screw axis intersects the pivot axis.

26. The assembly of claim 25, wherein the carriage axis is spaced from and parallel to the pivot axis; and wherein the carriage axis is spaced from and parallel to the output axis; and wherein the frame defines a longitudinal axis; and wherein the longitudinal axis is coaxial with the output axis.

27. The assembly of claim 25, wherein the screw axis moves with respect to the output axis.

* * * * *